United States Patent [19]
Ishi et al.

[11] 3,963,773
[45] June 15, 1976

[54] PROCESS FOR THE PRODUCTION OF PERACETIC ACID

[75] Inventors: Toshiharu Ishi, Otake; Akira Asahi, Yamaguchi; Hiroaki Fujita, Otake; Takeshi Sato, Otake; Nobusuke Urabe, Otake, all of Japan

[73] Assignee: Daicel, Ltd., Osaka, Japan

[22] Filed: June 13, 1974

[21] Appl. No.: 479,031

Related U.S. Application Data

[63] Continuation of Ser. No. 888,321, Dec. 29, 1969, abandoned.

[52] U.S. Cl. ............................ 260/502 A; 23/288 D
[51] Int. Cl.² ........................................ C07C 179/12
[58] Field of Search ................... 260/502 A, 502 R; 23/288, 283

[56] References Cited
UNITED STATES PATENTS 2,148,545  2/1939  Dorndorf et al. ..................... 23/288
3,228,977  1/1966  Sennewald et al. ............. 260/502 A

FOREIGN PATENTS OR APPLICATIONS 732,225  4/1966  Canada ........................... 260/502 A Primary Examiner—James O. Thomas, Jr.
Assistant Examiner—W. B. Lone
Attorney, Agent, or Firm—Woodhams, Blanchard & Flynn

[57] ABSTRACT

Peracetic acid is produced by the catalytic reaction of acetaldehyde with molecular oxygen or an oxygen containing gas by forwarding the reactants through an upright reaction vessel which is divided into at least three reaction zones by perforated partition plates in which the size of the perforations and the height of the reaction zones are selected so as to achieve an average gas flow velocity in the range of 0.4 – 6.0 m. per second at the perforations and a superficial gas flow velocity of 0.04 – 0.15 m. per second across the entire vessel.

5 Claims, 3 Drawing Figures

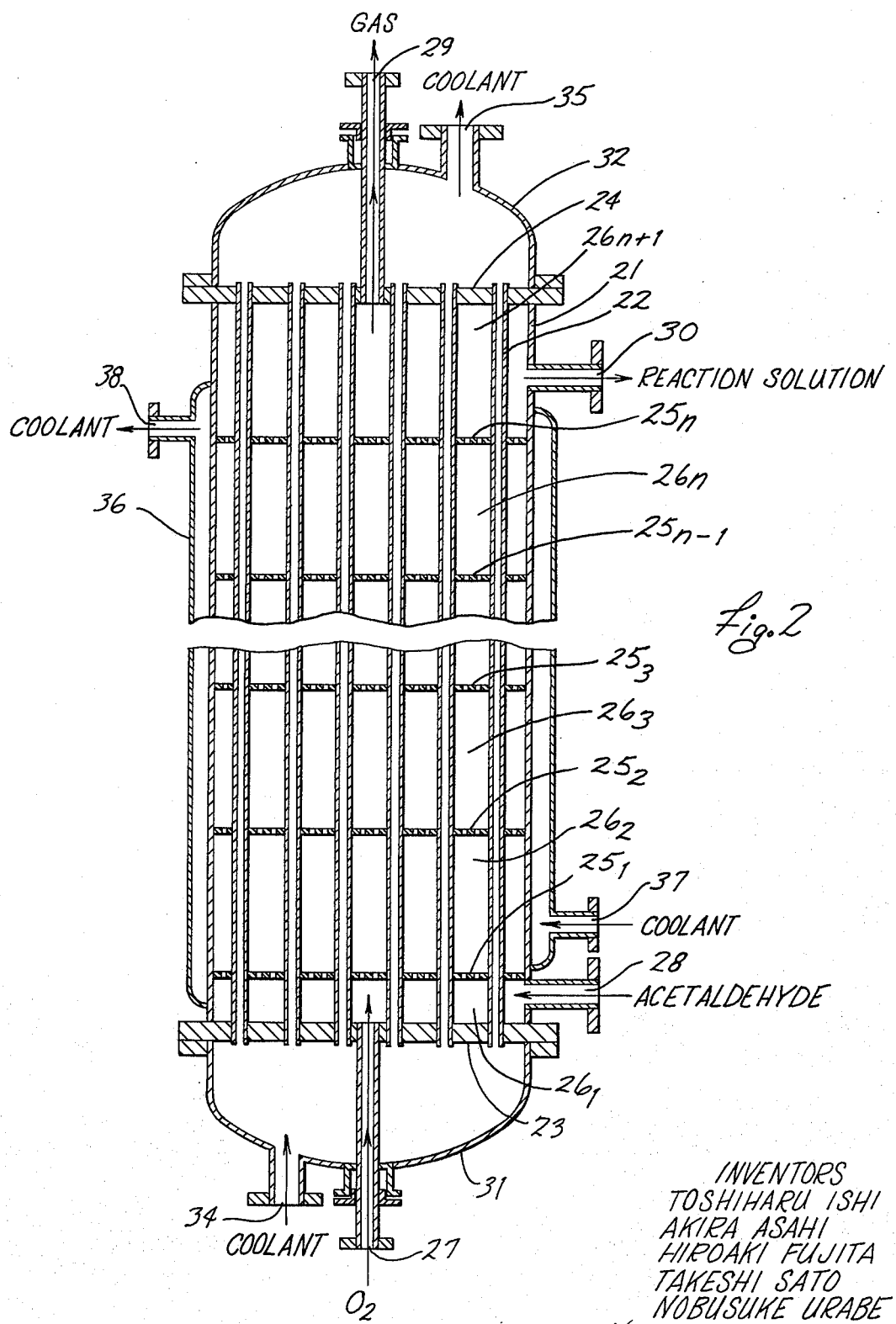

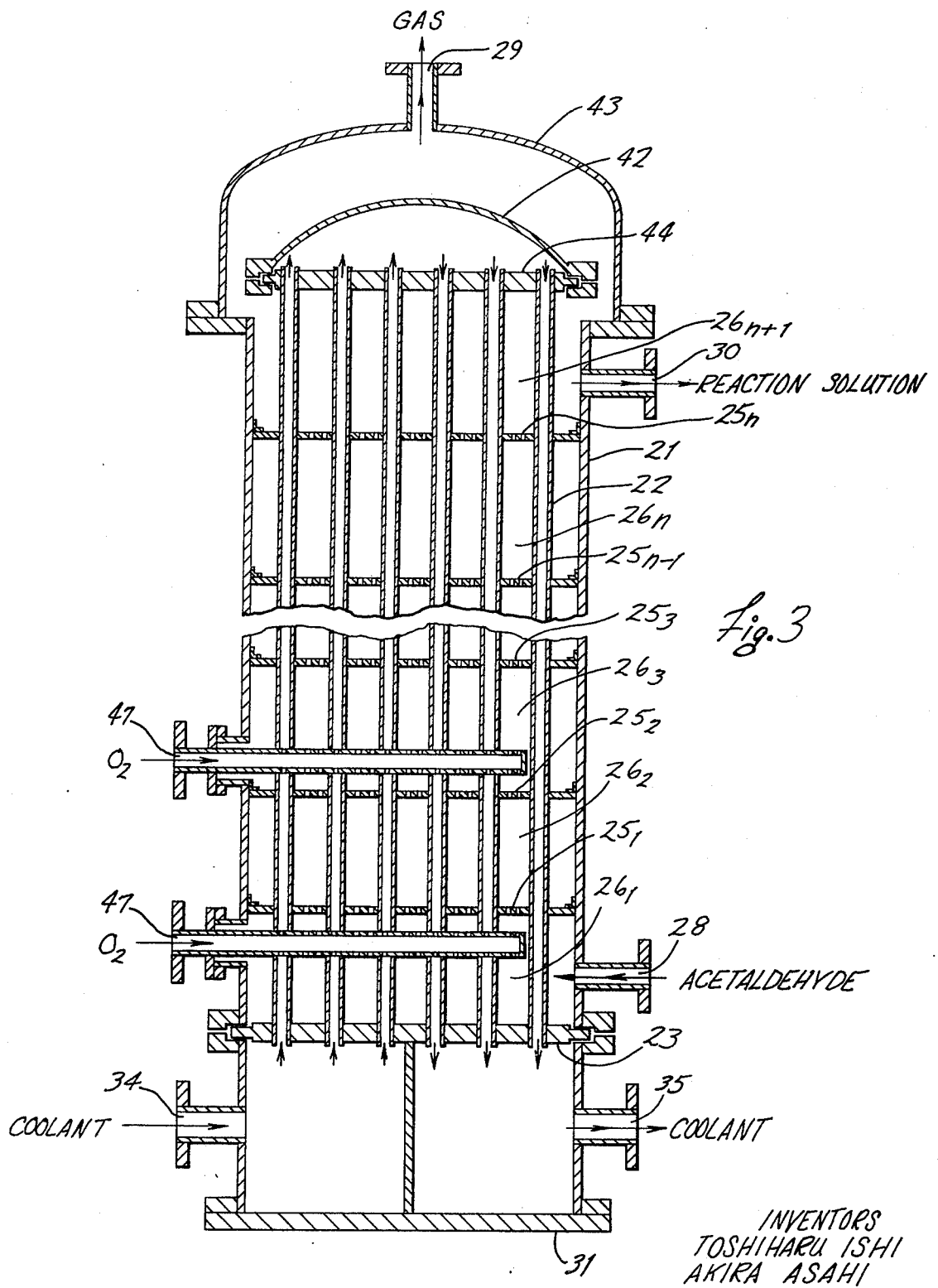

PROCESS FOR THE PRODUCTION OF PERACETIC ACID

This is a continuation of application Ser. No. 888,321, filed Dec. 29, 1969, now abandoned.

BACKGROUND OF THE INVENTION

1. Field of the Invention

This invention relates to an improvement in the process for producing peracetic acid by the liquid phase oxidation of acetaldehyde with oxygen or an oxygen-containing gas under atmospheric or superatmospheric pressure.

More particularly, this invention provides an economical and efficient process for the large scale production of peracetic acid in high yields. This invention overcomes two problems encountered in prior processes, namely, the provision of a large heat transfer area per unit volume of the reactor and the maintenance of good gas liquid contact. The solutions of these two problems have usually been considered to be incompatible with each other. In addition, the invention provides a substantially unidirectional or piston-like flow state in the reaction system.

2. Discussion of the Prior Art

It has been known in the art that peracetic acid can be produced by reacting oxygen or an oxygen-containing gas with a mixture of acetaldehyde and an organic solvent. For instance, German Patent No. 1,205,519 discloses a process wherein the said reaction is carried out under a total pressure of 10–100 atm. at a temperature of 20°–60° C. in the presence of a heavy metal salt, while maintaining the gas and liquid in a turbulent flow state, and various types of apparatus for carrying out this process are illustrated.

However, it is a matter of extreme difficulty, when carrying out this process using these types of apparatus on a large industrial scale, to establish compatibility between the removal of the oxidation reaction heat and good gas-liquid contact.

It has been made clear from a number of experimental results that the maintenance of a good gas-liquid contact state not only serves to promote the formation of peracetic acid, but also is necessary to avoid the by-production of acetic acid due to the successive reaction of the peracetic acid so formed with acetaldehyde. It is therefore not desirable, in view of the increased by-production of acetic acid and the consequent poor yield of peracetic acid with a reduced purity that would result, to use a cooling system external to and separate from the reactor for removing the reaction heat because the concentration of oxygen in the circulating reaction liquid becomes lowered to favor the formation of acetic acid. In a stirred tank-type reactor having no external reaction liquid circulation to a cooler, the bundle of cooling tubes or coils inserted inside the reactor for heat removal purposes often prevents the dispersion of bubbles throughout the tank so that the efficiency of gas-liquid contact becomes remarkably poor. It has also been proposed to use a bubble column or a jacketed small tubular coil-type reactor as an apparatus adapted for small scale production, but the application of these types of apparatus to large scale production is very troublesome, because several units of apparatus must be installed in parallel and the distribution of gas and liquid to each unit must be uniformly conducted.

We have made a comparative study of the data with respect to the above-mentioned various types of reactors, and have further carried out a detailed study on bubble column-type reactors for the purpose of achieving the efficient and economical manufacture of peracetic acid on a large scale in order that an improved bubble column-type reactor will be most suitable for attaining this purpose.

We have recognized, after conducting various experiments on small scale apparatus, that the use of a usual jacketed bubble column provides a lesser gas-liquid contact effect, i.e., a poorer reaction result, than the use of a reaction vessel provided with turbine-type stirring blades. The efficiency of the gas-liquid contact is further reduced if the removal of heat is conducted by inserting bundles of cooling tubes into a bubble column having a larger diameter. However, we have now discovered, after various experiments, that in order to overcome this difficulty, the maintenance of violent turbulent flow at every part within the column, while maintaining a substantially piston-like or unidirectional flow condition in the entire column, is most necessary for carrying out the reaction most efficiently. For this purpose, we have found that the use of a column-type reactor provided with vertical cooling tubes inserted therein and in which the shell side is used as the bubble column in combination with perforated partition plates provided so as to satisfy specific flow conditions, can attain an extremely advantageous result. The present invention is a result of this discovery.

SUMMARY OF THE INVENTION

Accordingly, the present invention relates to a process for producing peracetic acid by reacting acetaldehyde with gaseous oxygen or an oxygen-containing gas under atmospheric or super-atmospheric pressure, in which there is used a reactor comprising a vertical cylindrical vessel to which at least one vertical cooling tube is inserted as an inner tube. The reaction zone defined between the inner wall of said vessel and the outer wall of the inner tube is divided into at least three small reaction zones by at least two horizontal perforated partition plates provided, respectively, with a plurality of perforations, each perforation having an equivalent diameter of not more than 8 mm. (equivalent diameter = 4 × cross sectional area of the perforation ÷ circumferential length of the perforation). The height of said small reaction zone is 0.3 – 5.0 times the square root of its horizontal cross sectional area. The reaction is conducted by continuously introducing into the bottom small reaction zone a liquid mixture of acetaldehyde and an inert solvent and oxygen or an oxygen-containing gas, passing the liquid and gas through the perforations of each partition plate into the next upper small reaction zone while forming small bubbles in each small reaction zone by adjusting the mean flow velocity of the gas to be 0.4 – 6.0 m. per second at the perforations and to be 0.04 – 0.15 m. per second calculated as the column superficial velocity. The heat of reaction is removed by passing a liquid through said cooling tube. A reaction product liquid containing peracetic acid and a gas containing unreacted oxygen are withdrawn from the top small reaction zone.

The horizontal cross section of the vertical cylindrical reactor is usually circular, but it may be of oval or polygonal shape in certain cases. The cooling tubes inserted inside the vessel must necessarily be substantially vertical, because the desired sufficient gas-liquid contact will not be ensured if horizontal tubes, inclined tubes or coils are used in place of the vertical tubes, owing to the different gas-liquid flow condition that might result. Optionally, it is possible, however, to provide fins on the outer surface of the cooling tube for the purpose of increasing the heat transfer effect.

When a single vertical inner cooling tube is used, the annular space of the double tubular structure constitutes the reaction zone. When a plurality of vertical tubes are provided, the reaction zone is constituted by the shell side space of the multitubular structure. In the multitubular structure, the insertion of the bundle of tubes may be carried out by a system in which two fixed tube plates are fitted at the opposite ends of the tube, but a freely movable head system and a hair pin system (U-shaped tube system) may be employed as well. The attachment of a jacket on the exterior wall of the vessel is especially effective for increasing the cooling area when a double tubular structure is used, and it is also somewhat effective when a multitubular structure is used.

In order to ensure a sufficient gas-liquid contact effect in the reaction zone defined between the inner wall of the vessel and the outer wall of the inner tubes and to obtain satisfactory acetaldehyde conversion (the molar ratio of the aldehyde converted to the aldehyde fed) and peracid selectivity (the molar ratio of the peracid produced to the aldehyde converted) within a relatively short residence of time, it is necessary to divide the reaction zone into a plurality of small reaction zones by means of a plurality of a horizontal partition plates having a plurality of perforations. Also, it is necessary to take into consideration the combination of the diameter of the perforations, the distance between the partition plates and the flow speed conditions during the operation. The effect of the partition plates is to ensure good dispersion of the gas bubbles and turbulent agitation in the respective small reaction zones and to prevent the back-mixing of the liquid between adjacent small reaction zones to thereby maintain a substantially piston-like or uni-directional flow state within the entire reactor as a whole, although the flow in any individual reaction zone is not unidirectional.

The rate of peracetic acid formation is in proportion of 1.5th power of the concentration of acetaldehyde, and the rate of acetic acid formation is nearly in proportion to the concentrations of peracetic acid and acetaldehyde. Therefore, the closer to a piston-like flow state is maintained in the reactor, the shorter is the required reaction period to obtain the same acetaldehyde conversion and the less is the loss of peracetic acid, i.e., the less is the yield of the acetic acid by-product.

If the equivalent dimeter, as defined above, of the perforations of the partition plates exceeds 8 mm., the generation of bubbles will be concentrated at only a part of the perforations which not only results in preventing effective and uniform gas-liquid contact but also results in causing down-flow and back-mixing at other perforations, which will make the maintenance of the desired piston-like flow state impossible. The equivalent diameter of the perforations is preferably less than 5 mm. but the undesirable influence caused by the deflection or back-mixing of gas and liquid which will occur at equivalent diameters in the range of 5 - 8 mm. can be almost avoided by suitably selecting the height of the small reaction zones, i.e., the distance between the partition plates and the flow rates of the gas during the operation. There is no critical limit on the lower value of the equivalent diameter, but an equivalent diameter of less than 0.5 mm. is practically impossible due to the difficulty of mechanically drilling the perforations, and such a small perforation is rather useless because the bubble diameter will never be smaller than 1 mm. even when the gas is bubbled from very small perforations, such as one formed in a sintered metal plate. Accordingly, an equivalent diameter in the range of 2 - 5 mm. is usually preferable. When the distance between the partition plates is too small, the deflected flow of gas and liquid once formed will also affect the small reaction zones thereabove, but the undesirable influence of this deflected flow can be avoided by making the distance between adjacent partition plates to be more than 0.3 times the square root of the cross-sectional area of the small reaction zone, because this causes effective flow in a lateral or horizontal direction in order to overcome the bad influence of deflection. By making the distance between adjacent partition plates to be less than 5 times the square root of the cross-sectional area of the small reaction zone, the flow of rising bubbles formed will at least in substantial part be reversed so that they will in part descend or at least be prevented from unrestrained upward flow at the upper portion of the small reaction zone and they will scatter in every direction to result in a sufficient and uniform dispersion of the bubbles throughout the entirety of the small reaction zone. In order to achieve this result, however, the mean linear velocity of the gas must be more than 0.4 m. per second at the perforations, and more than 0.04 m. per second measured as the column superficial velocity. Flow rates less than the above range will sometimes cause insufficient reach of the reversed and descending flow to the bottom of the small reaction zone. On the contrary, too rapid a gas flow rate, i.e., as high as over 6 m. per second at the perforations, and above 0.15 m. per second measured as the column superficial velocity will cause the deflection of gas bubbles to the upper most small reaction zone, and hence is undesirable.

The maintenance of a piston-like or unidirectional flow state in the entire reaction system may also be obtained by connecting a plurality of complete mixing-type reactors in series, but it is economically more advantageous to obtain the same effect by dividing a single reactor with partition plates as proposed in the present invention.

The number of partition plates required for accomplishing the object of the invention is at least two, preferably at least five. The use of two or more reactors each having at least two partition plates and connected in series may be preferred in some cases. In order to avoid back-mixing through the perforations of partition plates, it is necessary to keep the flow of gas and liquid through the perforations in the partition plate in the same direction. In addition to the control of the diameters of the perforations and the flow rate conditions as described above, this can be accomplished by introducing both of the feed liquid mixture and the gas to the bottom small reaction zone.

The horizontal cross section of the perforations of the partition plates is usually circular, but it is not always limited to this shape. For example, if annular gaps are provided between the vertical inner tube or tubes and the partition plates such gaps may be used as the passages for the gas and liquid, that is, said gaps provide the perforations. In this case, the circumferential length of the perforations is the totality of the internal circumference of the perforations of the partition plate and the external circumference of the inner tube or tubes, and when they are each circular, the difference in the diameters of both circles corresponds with the equivalent diameter of the perforations.

The heights of the small reaction zones, i.e., the distance between the respective partition plates, need not be equal along the entire column. Since the difference in the reaction rates, that is, the degree of heat generation per unit volume between the adjacent small reaction zones is greater when reactant solution is closer to the feed inlet, the distance between the adjacent perforation plates may be set larger in the lower part of the reactor and set smaller in the upper part so as to reduce the temperature gradient to thereby improve the controlability of the reaction. For this purpose, there may be provided in the cooling fluid circuit a plurality of partitions to thereby change the temperature and flow rate of the cooling fuuid depending on the locations in the reaction zone, or the cooling area can be varied by the use of a hair-pin type multitubular structure. In another instance, a portion of the oxygen or oxygen-containing gas may be fed in at any intermediate small reaction zone instead of feeding the entire volume thereof at the bottom small reaction zone.

More appropriate temperature distribution can be obtained by dividing the total oxygen or oxygen-containing gas supplied into portions which are fed in at several reaction zones in addition to the bottom zone.

As the cooling fluid to be passed through the inner tube, water, brine and the like suitable cooling media having appropriate temperatures can be freely used. To increase the heat transfer coefficient by raising the flow rate of the cooling fluid is preferable for the control of the reaction.

The reaction product coming out of the top reaction zone will be treated to recover the desired product according to the manner known in the art. For instance, the reaction product will be separated into a gas and a liquid, if desired, and incorporated with a stabilizer and thereafter directly utilized for various reactions, or, if desired, it will be subjected to distillation under reduced pressure to remove unreacted acetaldehyde or catalyst to form a peracetic acid solution having a desired composition and stability.

The reaction conditions to be used for carrying out the process of this invention, i.e., the composition of the feed materials, temperature and pressure etc., are not limited within the range of the aforementioned German patent, and various other known conditions may be employed. For instance, the process of this invention may also be conducted under the condition of a relatively lower pressure, such as those disclosed in German Pat. No. 1,165,009 or Japanese Patent Publication No. 17190/1964, or under the condition of a high temperature reaction, such as is known in German Patent No. 1,269,120.

It will be understood that the particular solvent used the catalyst used form no part of the present invention and any suitable or conventional materials can be used.

The process of this invention will be further explained with reference to the attached drawings and following examples.

BRIEF DESCRIPTION OF THE DRAWINGS

The attached drawings are illustrative of several embodiments of the apparatus for carrying out the process of this invention.

In the drawings:

FIG. 2 is a cross-sectional view of an apparatus employing a multitubular structure having fixed tubes and plates in which the shell side is used as the reaction zone; and FIG. 3 is a cross-sectional view of a similar reactor of a multitubular structure having a freely movable head.

FIG. 1 illustrates an embodiment in which the annular part of the double tubular structure is used as the reaction zone. The upright cylindrical vessel 1 has a vertical tube 2 extending therethrough. In the annular portion formed between the vessel and the vertical tube, there are placed a number ($n$) of horizontal partition plates $3_1 - 3_n$ each having a number of perforations therethrough to thereby divide the annular portion into $n + 1$ sections $4_1 - 4_{n+1}$, each of which is used as a small reaction zone.

Figure 1:
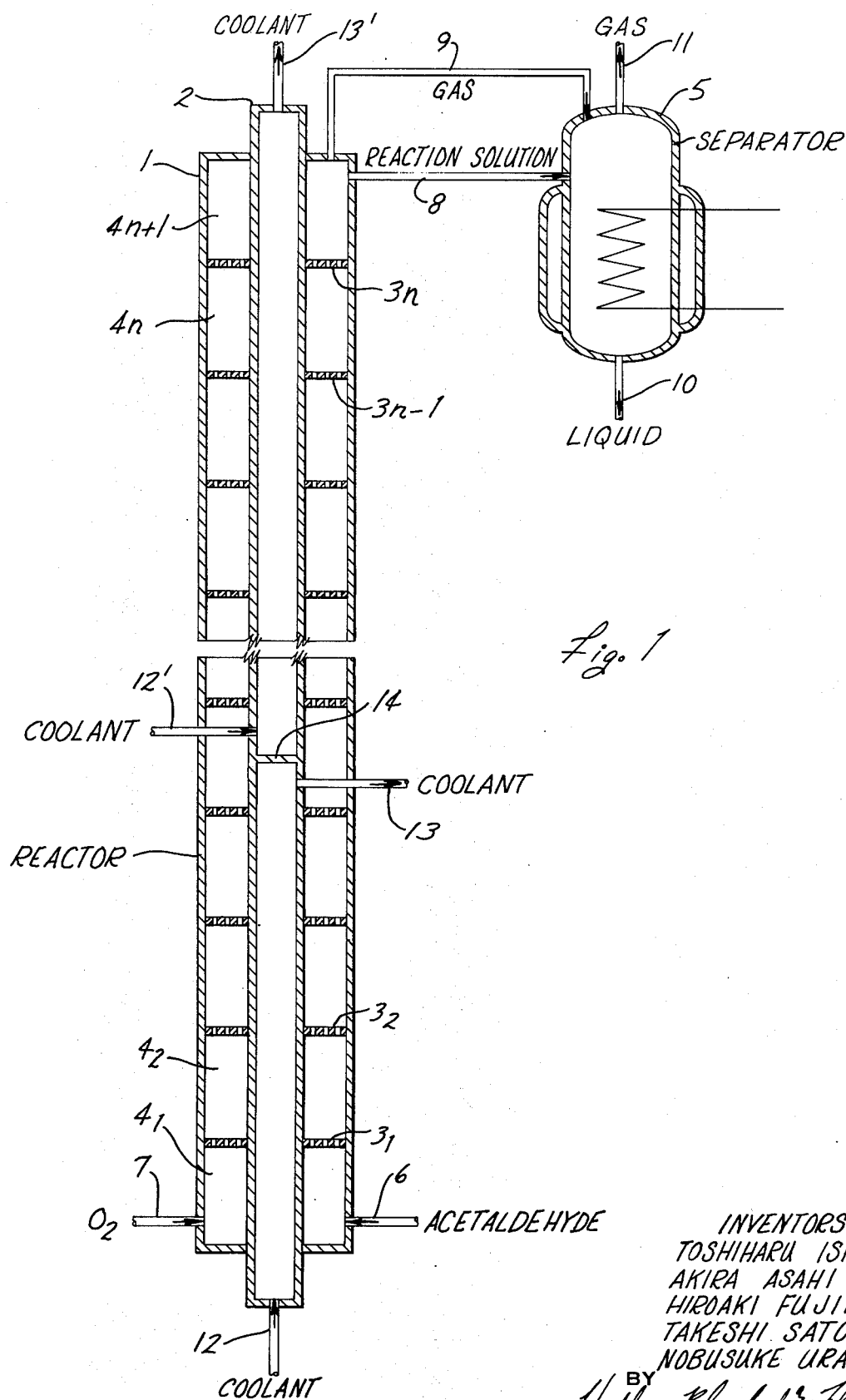
FIG. 1 is a cross-sectional view of an apparatus employing a double tubular structure in which the annular portion thereof is used as the reaction zone.

A solution of acetaldehyde and oxygen or an oxygen-containing gas are respectively fed continuously from the inlets 6 and 7 into the bottom reaction zone. In the embodiment shown in FIG. 1, the gas-liquid contact is rather incomplete in the bottom small reaction zone $4_1$, but the gas is further dispersed into fine bubbles at the small perforations of each partition plate as it ascends successively higher in gas-liquid concurrent flow in the reactor, so that a good gas-liquid contact can be ensured in the other small reaction zones $4_2 - 4_{n+1}$ so long as the perforation diameters of the partition plates, the height of the small reaction zones and the average gas flow velocity are kept within the aforementioned ranges.

From the top small reaction zones, a flow consisting mainly of a solution containing the produced peracetic acid and a flow consisting mainly of a gas containing unreacted oxygen are withdrawn from lines 8 and 9 respectively, and are passed to a gas-liquid separator 5 having a cooling surface. The gas after the separation is discharged from line 11 and is purged after the recovery of utilizable components by cooling, water scrubbing, etc., if desired.

The liquid after the separation is withdrawn through line 10 and is used as the product after adding a stabilizer or distilling under reduced pressure if necessary.

The cooling water enters the inner tube from lines 12 and 12' and leaves from 13 and 13' after removing the heat generated in the reaction zones. When partition plates 14 are inserted in the inner tube, inlets and outlets of the cooling water are provided for each section. The use of a plurality of cooling water circuits is preferred for attaining uniform temperature distribution in the reactor, but in some case the cooling water may be supplied from 12 and discharged from 13' by eliminating the partition plate 14.

In FIG. 2, there is illustrated an example of a multitubular structure having fixed tube plates at both its ends. The upright cylindrical vessel 21 has a number of vertical tubes 22 extending therethrough. The ends of the tubes are fixed to the tube plates 23, 24, which plates also serve as the end walls of the vessel. The shell side of the vessel is divided into $n + 1$ small reaction zones $26_1 - 26_{n+1}$ by a number of perforated partition plates $25_1 - 25_n$. The top and the bottom small reaction zones are provided with gas inlet 27, liquid inlet 28, gas outlet 29 and liquid outlet 30, respectively. Domes or end caps 31, 32 are fixed to the vessel body and are provided with a cooling water inlet 34 and outlet 35, respectively. An external cooling jacket 36 is attached to the outer wall of the vessel and is provided with a water inlet 37 and a water outlet 38.

In FIG. 3, there is illustrated an example of a free moving head type structure. The tube plate 44 and the dome 42 are not fixed to the vessel, so that the top covering of the vessel 43 must be separately assembled. A plurality of gas inlets 47 in the form of sparger pipes, each having a number of small perforations, are provided at several vertically spaced positions, in addition to the bottom small reaction zone, for supplying portions of the oxygen or oxygen-containing gas to different reaction zones so as to facilitate the uniform temperature distribution in the vessel.

The other reference numerals in FIG. 3 identify parts similar to those previously explained with reference to FIG. 2.

EXAMPLE 1

An upright cylindrical vessel as illustrated in FIG. 1 having an internal diameter of 10.2 cm., a height of 400 cm., an external diameter of the inner tube of 6.1 cm., 19 horizontal partition plates, each having 27 perforations per plate, and each perforation having a diameter of 0.3 cm. was used. To the bottom small reaction zone, 77 kg. per hour of a solution comprising 0.00035 wt. % cobalt acetate, 30.6 wt. % acetaldehyde and the balance ethyl acetate and 22 m³ per hour of compressed air (N.T.P.) were continuously introduced. The reaction to produce peracetic acid was conducted while maintaining the pressure at the reactor outlet at 30 kg/cm²G and controlling the temperature of the reaction zones to be at a maximum of 35°C. and a minimum of 28° C. by passing cooling water through the inner tube. The liquid continuously withdrawn after gas-liquid separation of the effluent from the top reaction zone contained, after steady-state constant conditions were achieved, 16.7% of peracetic acid and 0.37% of acetic acid. These results correspond to an acetaldehyde conversion of 32.5% and a peracetic acid selectivity of 97.4%.

EXAMPLE 2

Two vessels as illustrated in FIG. 2, each having an internal diameter of 24 cm. and a height of 290 cm. and provided with 62 inner tubes each having an internal diameter of 1.9 cm. and 7 horizontal partition plates each having 204 perforations, each perforation having a diameter of 0.3 cm., were connected in series. To the bottom small reaction zone, 667 Kg. per hour of a solution comprising 0.0003 wt.% cobalt acetate, 29.2 wt.% acetaldehyde and the balance ethyl acetate and 180 m³ per hour (N.T.P.) of compressed air were continuously fed in. The production of peracetic acid was conducted while maintaining the reactor outlet pressure at 25 Kg/cm²G. and the temperature of each reaction zone within the range of 30° – 35°C. The liquid flowing out of the top reaction zone contained, under steady state conditions, 13.4% peracetic acid and 0.54% acetic acid, which corresponds with an acetaldehyde conversion of 28.0% and a peracetic acid selectivity of 95.2%.

For the purpose of comparison, a solution containing 34.3% acetaldehyde was treated under similar reaction conditions using a turbine-type mixing tank of a volume of 100 liters. The acetaldehyde conversion of this test was 28% and the peracetic acid selectivity was 90.0%.

In the foregoing specification and the following claims, the following terms and derivatives thereof shall have the following meanings:

Average flow velocity of the gas at the perforations equals volumetric flow rate of gas into the column divided by cross-sectional areas of the perforations in any one partition plate.

Column superficial velocity equals volumetric flow rate of gas into the column divided by horizontal cross-sectional area of the reaction zone.

The embodiments of the invention in which an exclusive property or privilege is claimed are defined as follows:

1. In a process for the production of peracetic acid by the catalytic reaction of acetaldehyde with gaseous molecular oxygen or molecular oxygen-containing gas, in which a liquid mixture of acetaldehyde with an inert organic solvent and gaseous molecular oxygen or molecular-oxygen containing gas is fed into the bottom of an upright cylindrical reactor vessel means and is flowed upwardly therethrough to produce a reaction product containing peracetic acid, the improvement which comprises: employing upright cylindrical reactor vessel means containing therein internal upright cooling tube means spaced from the internal wall of the vessel means to provide a vertical reaction zone between the internal wall means of the vessel means and the external wall means of said cooling tube means, said reaction zone being divided into at least three small reaction zone sections by at least two horizontal partition plates each having a plurality of perforations therethrough, each perforation having an equivalent diameter (equivalent diameter = 4 × cross-sectional area of the perforation ÷ circumferential length of the perforation) of not more than 8 mm., the height of each small reaction zone section being in the range of from 0.3 to 5 times the square root of its horizontal cross-sectional area, continuously feeding into the bottom small reaction zone section (1) the liquid mixture of acetaldehyde with an inert organic solvent and (2) gaseous molecular oxygen or molecular oxygen-containing gas, flowing the liquid and the gas upwardly in series through the reaction zone sections in concurrent flow relationship, at an average flow velocity of the gas within the range of 0.4 – 6.0 m. per second through the perforations and within the range of 0.04 – 0.15 m. per second calculated as the superficial column velocity, with the liquid and gas passing upwardly in unidirectional flow through the perforations of each partition plate into the next higher small reaction zone section while forming and substantially uniformly dispersing the gas bubbles in the liquid in each small reaction zone section to effect turbulent agitation of the contents of each reaction zone section, removing the reaction heat by passing a coolant through the cooling tube means, and withdrawing from the uppermost reaction zone section a reaction product containing peracetic acid and a gas containing unreacted oxygen.

2. A process according to claim 1, in which the perforations each have an equivalent diameter of between about 2 – 5 mm.

3. A process according to claim 1, in which the reaction vessel means has at least five partition plates.

4. A process according to claim 1, in which the coolant tube means are divided into a plurality of sections and coolant is supplied to and removed from each section.

5. A process according to claim 1, in which the gas is fed from outside the reactor into at least two of said small reaction zone sections.

* * * * *